United States Patent [19]

Bailey et al.

[11] 4,338,393
[45] Jul. 6, 1982

[54] HETEROCYCLIC MAGENTA DYE-FORMING COUPLERS

[75] Inventors: Joseph Bailey, Bushey Heath; John Cook, Leighton Buzzard, both of England

[73] Assignee: Eastman Kodak Company, Rochester, N.Y.

[21] Appl. No.: 231,202

[22] Filed: Feb. 4, 1981

[30] Foreign Application Priority Data

Feb. 26, 1980 [GB] United Kingdom ............... 8006476

[51] Int. Cl.³ .................. G03C 7/00; G03C 1/40
[52] U.S. Cl. .................... 430/386; 430/387; 430/389; 430/472; 430/476; 430/548; 430/558
[58] Field of Search ............. 430/386, 387, 389, 472, 430/476, 548, 558

[56] References Cited

U.S. PATENT DOCUMENTS

| | | | |
|---|---|---|---|
| 3,649,278 | 3/1972 | Iwama et al. | 430/386 |
| 3,725,067 | 4/1973 | Bailey et al. | 430/476 |
| 3,733,335 | 5/1973 | Anderson | 430/386 |
| 4,061,498 | 12/1977 | Monbaliu et al. | 430/558 |
| 4,123,281 | 10/1978 | Monbaliu et al. | 430/544 |
| 4,130,427 | 12/1978 | Monbaliu et al. | 430/558 |
| 4,283,472 | 8/1981 | Gompf et al. | 430/558 |

*Primary Examiner*—J. Travis Brown
*Attorney, Agent, or Firm*—Joshua G. Levitt

[57] ABSTRACT

Photographic magenta dye-forming couplers have the general formula:

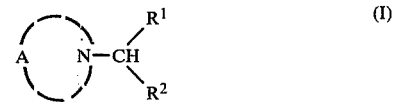

wherein:

A represents the atoms necessary to complete, with the nitrogen atom to which it is attached, a magenta dye-forming coupler moiety whose coupling position is inactivated by the —$CHR^1 R^2$ group;

$CHR^1 R^2$ is a blocking group which, upon reaction with oxidized color developing agent, is detached from the coupler moiety to yield a mobile reaction product;

$R^1$ is alkyl—O—CO—, alkyl—CO—, aryl—O—CO—, aryl—CO—, —COOH, —$NO_2$ or —CN and $R^2$ is a group specified for $R^1$ or aryl—NHCO—.

These couplers can be incorporated in photographic elements, emulsions and processing compositions.

8 Claims, No Drawings

HETEROCYCLIC MAGENTA DYE-FORMING COUPLERS

This invention relates to novel magenta dye-forming couplers, to photographic silver halide emulsions and elements containing these couplers and to processes of forming magenta dye images with these couplers.

Color images are obtained in conventional color photographic materials by reaction between the oxidation product of a silver halide color developing agent (i.e., oxidized aromatic primary amino developing agent) and a dye forming compound known as a coupler. The reaction between coupler and oxidized color developing agent results in coupling of the oxidized color developing agent at a reactive site in the coupler, known as the coupling position, and yields a dye. The dyes produced by coupling are indoaniline, azomethine, indamine, or indophenol dyes, depending upon the chemical composition of the coupler and the developing agent. The subtractive process of color formation is ordinarily employed in multicolored photographic elements and the dyes produced by coupling are usually cyan, magenta and yellow dyes which are formed in or adjacent silver halide emulsion layers sensitive to radiation absorbed by the image dye, i.e., silver halide emulsion layers sensitive to the red-, green- or blue-regions of the spectrum. Among the couplers employed to produce magenta dyes are pyrazolotriazoles, pyrazolobenzimidazoles, indazoline-3-ones, and pyrazolones.

Many of the dye-forming couplers employed in photographic materials are 4-equivalent couplers. In other words, they require development of four molecules of silver halide in order ultimately to produce one molecule of dye. Also known are 2-equivalent, 6-equivalent and 8-equivalent couplers which require development of two, six or eight molecules of silver halide, respectively, to produce one molecule of dye.

Since 2-equivalent couplers yield more dye per unit developed silver than higher equivalent couplers, they frequently are preferred for use in photographic elements. However, there are instances where the higher dye yield associated with 2-equivalent couplers is not desired. While the amount of dye formed could be reduced by using less silver, this would result either in a loss in photographic speed if the silver halide grain size is not modified, or in increased graininess if larger silver halide grains are employed to compensate for the speed loss.

One solution would be to employ 4-equivalent couplers rather than 2-equivalent couplers. However, in some instances the group which is eliminated from 2-equivalent couplers on coupling, and which is responsible for their lower equivalency, confers desirable properties on the coupler or leads to desirable effects in the layer in which it is released or in adjacent layers. Thus, there are instances where it is useful to employ 2-equivalent couplers which would provide a dye yield comparable to that obtained with 4-equivalent couplers. In other instances, it is useful to obtain an even lower dye yield.

Another solution would be to employ compounds known as competing couplers. These are compounds which compete with dye-forming couplers for oxidized silver halide developing agent but do not result in dye density in the processed photographic element. However, if employed in the developer composition these competing couplers can act on all silver halide emulsion layers in the element rather than just on the layer where reduced dye yield is desired. If the competing coupler is ballasted and incorporated in a layer of the element it can unduly increase the thickness of the layer, resulting in a loss in sharpness in underlying layers.

We have found novel 4- and 6-equivalent magenta dye-forming couplers. The 4-equivalent couplers of our invention contain coupling-off groups contained in 2-equivalent couplers and, therefore, can provide the advantages associated with such groups. Both the 4-equivalent and 6-equivalent couplers permit a separate competing coupler to be dispensed with and thus avoid the limitations associated with competing couplers. Further, preferred couplers of this invention are less sensitive to aerial contaminants, such as formaldehyde, than are commonly employed pyrazolone magenta dye-forming couplers.

In one embodiment, this invention relates to novel magenta dye-forming couplers as described below.

In another embodiment, this invention relates to photographic silver halide emulsions and elements containing the novel magenta dye-forming couplers.

In yet another embodiment, this invention relates to processes of forming magenta dye images by developing a photographic element in the presence of the novel magenta dye-forming couplers.

The novel magenta dye-forming couplers of the present invention can be represented by the formula:

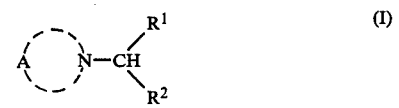

wherein:

A represents the atoms necessary to complete, with the nitrogen atom to which it is attached, a magenta dye-forming coupler moiety whose coupling position is inactivated by the —CHR$^1$R$^2$ group;

CHR$^1$R$^2$ is a blocking group which, upon reaction with oxidized color developing agent is detached from the magenta dye-forming coupler moiety to yield a mobile reaction product;

R$^1$ is alkyl—O—CO—, alkyl—CO—, aryl—O—CO—, aryl—CO—, —COOH, —NO$^2$ or —CN; and R$^2$ is a group specified for R$^1$ or aryl—NHCO—.

The attachment of the —CHR$^1$R$^2$ blocking group to the nitrogen atom of the magenta dye-forming coupler moiety completed by A inactivates the coupling position of the coupler moiety by preventing ionization (proton removal) at the coupling position. Thus, until the blocking group is detached, the magenta dye-forming coupler moiety is incapable of reacting with oxidized color developing agent to form dye. The methylene group in the CHR$^1$R$^2$ blocking group is activated by adjacent electron withdrawing groups and, thus, the blocking group is capable of reacting with oxidized color developing agent. In fact, the blocking group will generally be a diffusible yellow dye-forming coupler and will react with oxidized color developing agent to form a mobile yellow dye.

Reaction of the blocking group with oxidized color developing agent detaches it from the magenta dye-forming coupler moiety, thereby activating the latter moiety and enabling it to react with oxidized color developing agent to form a magenta dye. Detachment of the blocking group requires reactions which consume two equivalents of silver. Reaction of the magenta dye-forming coupler moiety with oxidized color developing agent to form a dye consumes an additional two or four equivalents of silver, depending upon the moiety in the coupling position. Since the blocking group yields a mobile reaction product which is removed from the element during processing and, hence, does not contribute to dye density, a total of 4 or 6 equivalents of silver are required to produce one molecule of magenta dye in the element.

The magenta dye-forming coupler moiety completed by A can be derived from any of the heterocyclic magenta dye-forming couplers known in the art which contain a nitrogen atom available for blocking. Preferred magenta dye-forming coupler moieties are pyrazolotriazoles, pyrazolobenzimidazoles and indazolin-3-ones.

The alkyl portion of the $R^1$ and $R^2$ groups are preferably substituted or unsubstituted alkyl groups of 1 to 6 carbon atoms, e.g., methyl, ethyl, propyl, isopropyl, butyl, tertiary butyl, amyl and hexyl. The aryl portion of the $R^1$ and $R^2$ groups are preferably aryl groups of 6 to 12 carbon atoms, e.g., phenyl, naphthyl, tolyl and xylyl. Preferred substituents for both the alkyl and aryl portions of the $R^1$ and $R^2$ groups are water solubilizing substituents, e.g., carboxy, esterified carboxy, sulfo and hydroxy.

When intended for incorporation in a photographic element the coupler should be nondiffusible. This can be accomplished by employing a ballasted magenta dye-forming coupler moiety; i.e., a moiety of sufficient bulk that it will not diffuse through the alkali-permeable layers of the element during processing. Conversely, when intended for incorporation in a developer composition the coupler should be of such size that it will diffuse through the alkali-permeable layers of the element. In both cases the $CHR^1R^2$ group should, upon reaction with oxidized color developing agent and detachment from the magenta dye-forming coupler moiety, yield a mobile reaction product which will diffuse out of the element during further processing. This can be accomplished by limiting the size of the $R^1$ and $R^2$ groups, and/or incorporating solubilizing groups in them.

Particularly preferred couplers are those in which the coupler moiety completed by A is a pyrazolotriazole, pyrazolobenzimidazole or indazolin-3-one moiety represented by one of the following formulae, in which the unsatisfied bond shows the point of attachment of the —$CHR^1R^2$ group and the asterisk (*) denotes the coupling position:

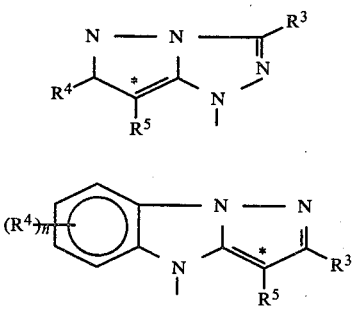

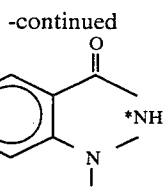

wherein:
$R^3$ and each $R^4$ are independently alkyl, aryl, heterocyclyl, amino, acylamido, hydroxy, alkoxy, alkylthio, carboxy or esterified carboxy;
$R^5$ is hydrogen or a coupling-off group which splits off during color development; and
n is 0, 1 or 2.

Examples of suitable $R^3$ and $R^4$ groups are: straight or branched chain, substituted or unsubstituted alkyl, preferably containing 1 to 30 carbon atoms, e.g., methyl, ethyl, n-propyl, isopropyl, sec-butyl, tert-butyl, tert-pentyl, n-hexyl, n-dodecyl, n-heptadecyl, n-docosyl, 2-chloro-n-butyl, 2-hydroxyethyl, 2-phenylethyl, 3-(3-acylamidophenyl)propyl, 2-(2,4,6-trichlorophenyl)ethyl and 2-aminoethyl; substituted or unsubstituted aryl, preferably containing 6 to 45 carbon atoms, e.g., phenyl, α- or β-napthyl, 4-methylphenyl, 2,4,6-trichlorophenyl, 3,5-dibromophenyl, 2-, 3- or 4-trifluoromethylphenyl, 2-chloro-α-naphthyl, 3-α-naphthyl, 2-methoxyphenyl, 2-acylamidophenyl and 3,5-(2,4-di-tert-amylphenoxyacetamido)-2,4,6-trimethylphenyl; heterocyclyl, e.g., pyridyl or thienyl; substituted or unsubstituted, primary, secondary or tertiary amino e.g., amino, methylamino, diethylamino, n-docosylamino, phenylamino, tolylamino, 4-(3-sulphobenzamido)anilino, 4-cyanophenylamino, 2-trifluoromethyl-phenylamino and benzothiazoloamino; acylamido e.g., ethylcarbonamido, n-decylcarbonamido, phenylethylcarbonamido, phenylcarbonamido, 2,4,6-trichlorophenylcarbonamido, 4-methylphenylcarbonamido, 2-ethoxyphenylcarbonamido, 2,4-di-tert-amylphenoxyalkylcarbonamido, 2-[(2,4-di-tert-amylphenoxy)acetamido]benzamido, α- or β-naphthylcarbonamido, 2,4-di-tert-amylphenoxy-n-butylsulfonamido, and non-coupling phenolic stabilizer moieties as described in Lestina U.S. Pat. No. 3,519,429; hydroxy substituted or unsubstituted alkoxy of 1 to 22 carbon atoms, e.g., methoxy, ethoxy, n-butyloxy, n-hexoxy, n-dodecyloxy and n-docosoxy; and carboxy or esterified carboxy of 2 to 22 carbon atoms, e.g., methoxycarbonyl, ethoxycarbonyl, n-docosoxycarbonyl and phenoxycarbonyl.

The coupling-off groups represented by $R^5$ can be any of the coupling-off groups known in the art. Such groups can alter the equivalency of the coupler, can modify the reactivity of the coupler, or can advantageously affect the layer in which the coupler is coated or other layers in the element by performing, after release from the coupler, such functions as development inhibition, bleach inhibition, bleach acceleration, color correction and the like. Representative coupling-off groups include halogen, alkoxy, aryloxy, heterocyclyloxy, sulfonyloxy, acyloxy acyl, heterocyclyl, thiocyano, alkylthio, arylthio, heterocyclylthio, sulfonamido, phosphonyloxy and arylazo.

Structures of representative couplers of this invention are shown below. In these structures the following abbreviations are employed:
Me for methyl;

Ph for phenyl;
t-Bu for tertiary butyl; and
Et for ethyl.
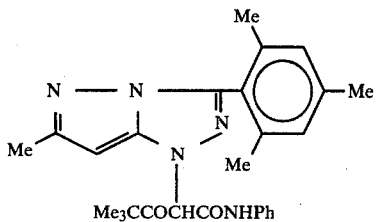
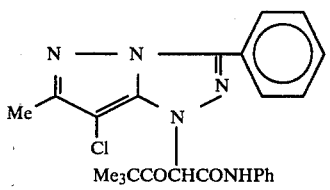
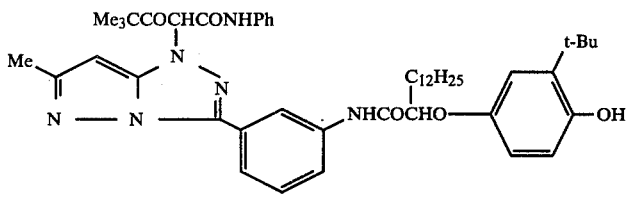
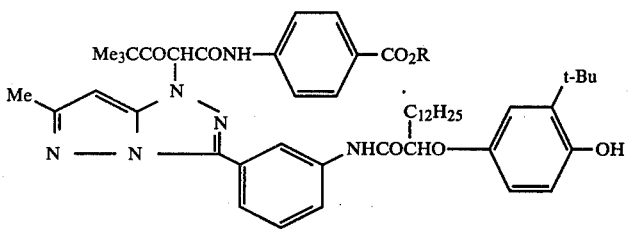
where R is Et or H
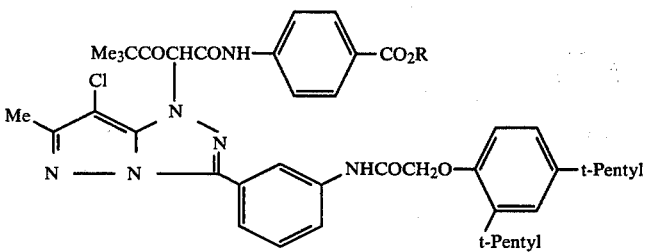
where R is Et or H
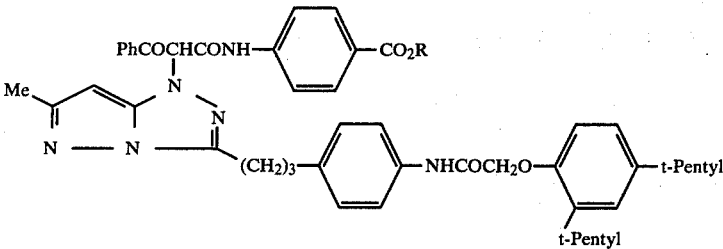
where R is Me or H

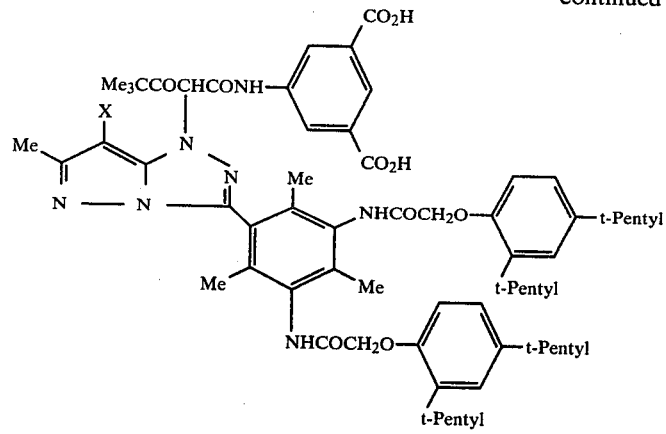
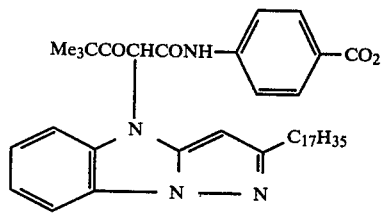
where X is H, Cl, or
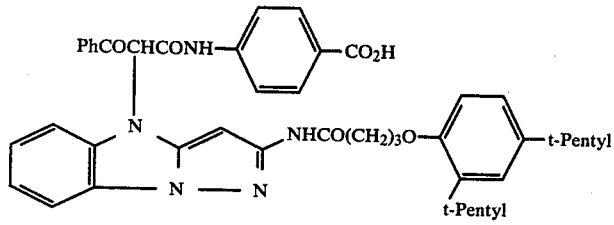
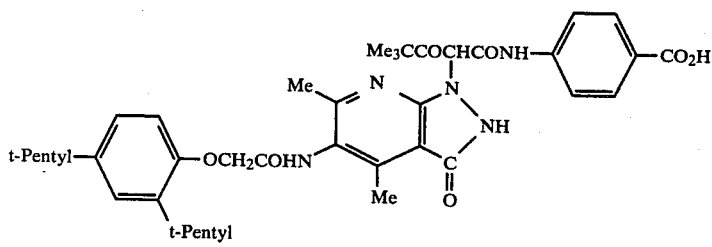
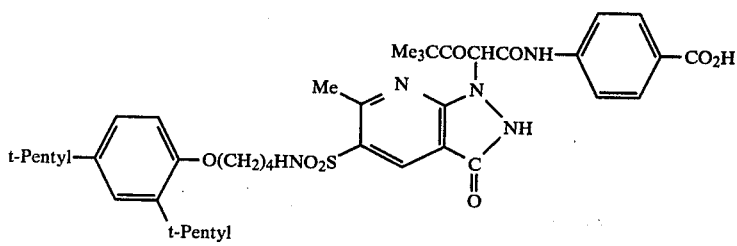
the present couplers can be prepared by condensing compounds of the formulae:

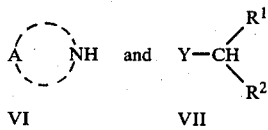

VI         VII wherein:

Y is halogen, e.g., Cl or Br, and

A, $R^1$ and $R^2$ are as defined above, in a solvent and in the presence of a base. The preferred solvents are hexamethylphosphoric triamide and dimethylformamide. The preferred base is sodium methoxide. It may be convenient to block the coupling position on the coupler of formula VI prior to this condensation, e.g. by making $R^5$ in formulae II and III an ester group. This can be removed by hydrolysis after the condensation reaction.

The magenta dye-forming couplers of this invention can be used in the ways and for the purposes that magenta dye-forming couplers have been previously used in the photographic art. The couplers can be incorporated in silver halide photographic elements or in photographic developer compositions so that during development they will be present to react with oxidized color developing agent.

When incorporated in photographic elements, the couplers preferably are incorporated in silver halide emulsions of the photographic element. Alternatively, the couplers can be incorporated in photographic elements in a layer adjacent the silver halide emulsion where, during development, the coupler will be in reactive association with development products such as oxidized color developing agent. Thus, as used herein, the term "associated therewith" signifies that the coupler is in the silver halide emulsion layer or in an adjacent location where, during processing, it will come into reactive association with silver halide development products.

The photographic elements can be single color elements or multicolor elements. In a multicolor element, the magenta dye-forming couplers of this invention would usually be associated with a green-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units can be arranged in various orders as known in the art. In an alternative format, the emulsions sensitive to each of the three primary regions of the spectrum can be disposed as a single segmented layer, e.g., as by the use of microvessels or cells as described in Whitmore U.S. patent application Ser. No. 8,819 filed Feb. 2, 1979.

A typical multicolor photographic element would comprise a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, at least one of the magenta dye-forming couplers being a coupler of this invention, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Research Disclosure, December 1978, Item 17643, published by Industrial Opportunities Ltd., Homewell Havant, Hampshire, PO9 1EF, U.K., the disclosures of which are incorporated herein by reference. This publication will be identified hereafter as "Research Disclosure."

The silver halide emulsions employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. The couplers of this invention and any additional couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a developer composition containing a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-N,N-diethylaniline hydrochloride, 4-amino-3-methyl-N-ethyl-N-β-(methanesulfonamido)ethylanilinesulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxy-ethyl)-m-toluidine di-p-toluene sulfonic acid.

With negative working silver halide this processing step leads to a negative image. To obtain a positive (or reversal) image, this step can be preceded by development with a nonchromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following examples further illustrate this invention.

EXAMPLE 1—Preparation of Coupler No. 1

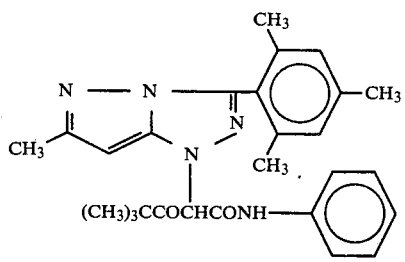

A mixture of mesityl-6-methyl-1H-pyrazolo[3,2-c]-s-triazole (Compound A) (2.4 g, 0.01 mole) in hexamethylphosphoric triamide (HMPT) (20 ml) containing 2-bromo-2-pivaloyl acetanilide (Compound B) (2.72 g, 0.01 mole) and sodium methoxide (0.51 g, 0.01 mole) was stirred at 80° C. for 3 hours. The mixture was cooled and poured into crushed ice (200 g) containing 12 M hydrochloric acid (10 ml) and stirred for 30 minutes. The resulting solid was filtered off, dried in vacuo and chromatographed on silica gel (300 g) eluting with toluene/ethyl acetate (98:2). The desired product (Coupler No. 1) was obtained as an oil (2.5 g) and then crystallized from ligroine (petroleum ether, boiling point 60°–80° C.); yield 1 g, m.p. 155°–6° C.

$C_{27}H_{31}N_5O_2$ Requires: C, 70.9; H, 6.8; N, 15.3. Found: C, 70.6; H, 6.9; N, 15.2%.

PMR, IR and mass spectral data were consistent with the structure of Coupler No. 1.

EXAMPLE 2—Preparation of Coupler No. 2

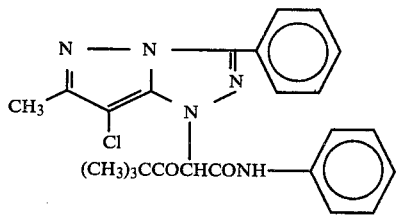

A mixture of 1-(N)-acetyl-7-chloro-6-methyl-3-phenyl-1-H-pyrazolo[3,2-c]-s-triazole (Compound C) (0.275 g, 0.001 mole) in HMPT (2 ml) containing 2-bromo-2-pivaloylacetanilide (Compound B) (0.272 g, 0.001 mole) and sodium methoxide (120 mg) was heated on a steam bath for 4 hours. The mixture was poured into 3 N hydrochloric acid (2 ml) and partitioned three times into 20 ml portions of ethylacetate. The ethyl acetate portions were combined, dried over magnesium sulfate and evaporated to yield a gum (140 mg). Chromatography on thin layer (preparative) silica gel plates (20×20×0.2 cm), eluting with toluene/ethyl acetate (98:2), yielded Coupler No. 2 as a gum (80 mg); one spot by TLC. The product was characterized by its accurate mass spectrum.

$C_{24}H_{24}ClN_5O_2$ Requires: M=449.161842. Found: $M^+$=449.162188.

EXAMPLE 3

Coupler No. 1, (10 mg), prepared as in Example 1, in a mixture of 10% aqueous sodium carbonate (5 ml) and methanol (0.5 ml) was treated with 4-amino-3-methyl-N,N-diethylaniline hydrochloride developing agent (10 mg) and potassium persulphate oxidizing agent (10 mg) and then warmed on a steam bath for 1 minute. The resulting dyes were extracted into ethyl acetate (5 ml), the ethyl acetate layer was washed with (1) 10 ml water containing one drop of concentrated nitric acid, and then (2) distilled water.

This procedure was repeated for the individual starting compounds (A) and (B). The wavelength(s) of absorption maxima ($\lambda_{max}$) and halfband widths (HBW) of the dyes obtained from Coupler No. 1 and Compounds A and B were measured in ethyl acetate with the following results:

| Coupler/Compound | $\lambda_{max}$ | HBW (nm) |
| --- | --- | --- |
| 1 | 533, | 58 |
|   | 431 | * |
| A | 534 | 60 |
| B | 430 | 130 |

*Could not be measured.

Mixing solutions of the dyes from Compounds A and B gave a composite absorption spectrum which was essentially the same as that of the dyes from Coupler No. 1.

EXAMPLE 4

The procedure of Example 3 was repeated with Coupler No. 2 prepared as in Example 2. The absorption spectrum of the dyes from Coupler No. 2 could be simulated by mixing solutions of dyes from Compounds B and C. The wavelength(s) of absorption maxima and halfband widths were as follows:

| Coupler/Compound | $\lambda_{max}$ (nm) | HBW (nm) |
| --- | --- | --- |
| 2 | 428, | * |
|   | 550 |   |
| B | 429 | 130 |
| C | 550 | 84 |

*Could not be measured.

Examples 3 and 4 illustrate that couplers of this invention will react with oxidized silver halide developing agent to yield a magenta dye and a yellow dye. The yellow dye obtained in these examples is of low molecular weight and bulk and analogues thereof containing water-solubilising groups will be washed out of a photographic element during photographic processing by the processing solutions.

EXAMPLE 5—Preparation of Coupler No. 3 (R=H)

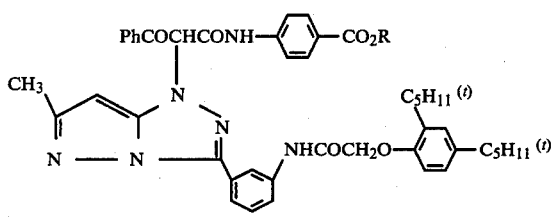

2-Benzoyl-2-bromo-p-ethoxycarbonylacetanilide was condensed with 6-methyl-3-m-nitrophenyl-1H-pyrazolo-[3,2-c]-s-triazole in HMPT in the presence of 8 equivalents of sodium methoxide at 80° C. for 3 hours analogously to the preparation of Coupler No. 1. The yield of product was 36%.

The resulting nitro containing coupler was hydrogenated in tetrahydrofuran in the presence of Pd/C Catalyst to give in 98% yield the corresponding amino compound.

This amine was condensed with 2,4-ditertiarypentyl-phenoxyacetyl chloride in dimethylformamide in the presence of dimethylaniline to give the ester (i.e. the above structure where R=ethyl). Hydrolysis of the ester was accomplished by treatment with 10% KOH in methanol at 20° C. for 2 hours to yield Coupler No. 3 where R=H in the above structure.

Coupler 3 may be incorporated with photographic materials where it will produce on development, a nondiffusible magenta dye and a yellow dye that will be washed out of the material.

This invention has been described in detail with particular reference to certain preferred embodiments thereof, but it will be understood that variations and modifications can be effected within the spirit and scope of the invention.

What is claimed is:

1. A photographic element comprising a support and a photosensitive silver halide emulsion having associated therewith a nondiffusible magenta dye-forming coupler of the formula:

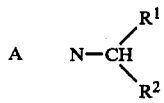

wherein
A represents the atoms necessary to complete, with the nitrogen atom to which it is attached, a ballasted pyrazolotriazole, pyrazolobenzimidazole or indazolin-3-one magenta dye-forming coupler moiety whose coupling position is inactivated by the —CHR¹R² group;
CHR¹R² is a blocking group which, upon reaction with oxidized color developing agent, is detached from the magenta dye-forming coupler moiety to yield a mobile reaction product;
R¹ is alkyl—O—CO—, alkyl—C0—, aryl—O—CO—, aryl—C0—, —COOH, —NO₂ or —CN; and
R² is a group specified for R¹ or aryl—NHCO—.

2. A photographic element of claim 1 wherein at least one of R¹ and R² contains an alkyl or aryl group substituted with one or more carboxy, sulfo or hydroxy groups.

3. A photographic element of claims 1 or 2 wherein A completes a pyrazolotriazole magenta dye-forming coupler moiety.

4. A photographic element of claim 1 in which A completes a magenta dye-forming coupler moiety having one of the following formulae, in which the unsatisfied bond is the point of attachment of the —CHR¹R² group:

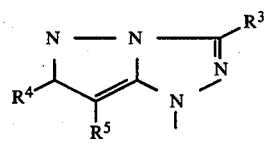

II

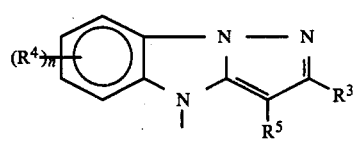

III

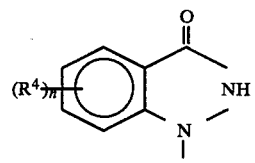

IV wherein:
R³ and each R⁴ are independently alkyl, aryl, heterocyclyl, amino, acylamido, hydroxy, alkoxy, alkylthio, carboxy or esterified carboxy,
R⁵ is hydrogen or a coupling-off group; and
n is 0, 1 or 2.

5. A photographic element of claim 1 wherein the magenta dye-forming coupler has one of the structures:

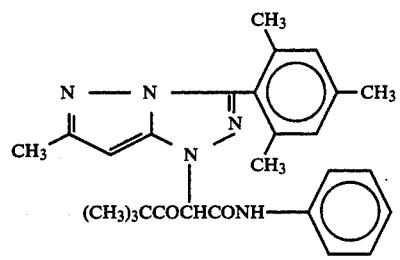

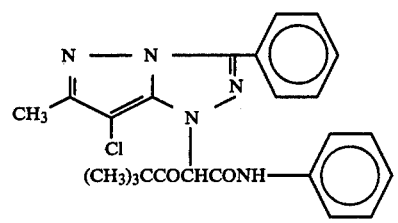

6. A process of forming a magenta dye image in a photographic element comprising a support and an imagewise exposed silver halide emulsion, comprising the step of developing the element with a developer composition containing a color developing agent in the presence of a magenta dye-forming coupler having the structure:

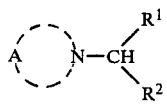

wherein:

A represents the atoms necessary to complete, with the nitrogen atom to which it is attached, a pyrazolotriazole, pyrazolobenzimidazole or indazolin-3-one magenta dye-forming coupler moiety whose coupling position is inactivated by the —CHR$^1$R$^2$ group;

CHR$^1$R$^2$ is a blocking group which, upon reaction with oxidized color developing agent, is detached from the magenta dye-forming coupler moiety to yield a mobile reaction product;

R$^1$ is alkyl—O—CO—, alkyl—CO—, aryl—O—CO—, aryl—CO—, —COOH, —NO$_2$ or —CN; and R$^2$ is a group specified for R$^1$ or aryl—NHCO—.

7. A process of claim 6 wherein the coupler is nondiffusible and is initially present in the element.

8. A process of claim 6 wherein the coupler is diffusible and is initially present in the developer composition.

* * * * *

UNITED STATES PATENT AND TRADEMARK OFFICE
CERTIFICATE OF CORRECTION

PATENT NO. : 4,338,393
DATED : July 6, 1982
INVENTOR(S) : Joseph Bailey and John Cook It is certified that error appears in the above-identified patent and that said Letters Patent are hereby corrected as shown below:

Formula in Claim 1, column 13, between lines 45-50, please complete formula by adding broken circle between A and N;

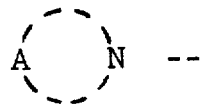

line 62, delete "alkyl-CO-" and insert --alkyl-CO- --;
line 63, delete "aryl-CO-" and insert --aryl-CO- --.

Signed and Sealed this

Twenty-first Day of September 1982

[SEAL]

Attest:

Attesting Officer

GERALD J. MOSSINGHOFF

Commissioner of Patents and Trademarks